United States Patent
Collins, Sr. et al.

(10) Patent No.: US 10,295,447 B2
(45) Date of Patent: May 21, 2019

(54) RAPID ENERGIZED DISPERSIVE SOLID PHASE EXTRACTION (SPE) FOR ANALYTICAL ANALYSIS

(71) Applicant: CEM Corporation, Matthews, NC (US)

(72) Inventors: Michael J. Collins, Sr., Matthews, NC (US); Joseph J. Lambert, Charlotte, NC (US); Matthew N. Beard, Huntersville, NC (US); Paul C. Elliott, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 69 days.

(21) Appl. No.: 15/644,950

(22) Filed: Jul. 10, 2017

(65) Prior Publication Data

US 2019/0011339 A1    Jan. 10, 2019

(51) Int. Cl.
*G01N 30/06* (2006.01)
*G01N 1/40* (2006.01)

(52) U.S. Cl.
CPC ......... *G01N 1/4055* (2013.01); *G01N 1/4022* (2013.01); *G01N 2001/4061* (2013.01); *G01N 2030/062* (2013.01)

(58) Field of Classification Search
CPC .................. G01N 1/4055; G01N 2001/4061
See application file for complete search history.

(56) References Cited

U.S. PATENT DOCUMENTS

| | | | |
|---|---|---|---|
| 2,643,940 | A | 6/1953 | Stevens |
| 4,265,860 | A | 5/1981 | Jennings |
| 4,429,049 | A | 1/1984 | Rogers |
| 5,017,500 | A | 5/1991 | Langer |
| 5,268,103 | A | 12/1993 | Jameson |
| 5,272,094 | A | 12/1993 | Barker |
| 5,344,571 | A | 9/1994 | Mendershausen |
| 5,447,077 | A | 9/1995 | Lautenschlager |

(Continued)

FOREIGN PATENT DOCUMENTS

| | | |
|---|---|---|
| AU | 2018204538 | 8/2018 |
| CN | 106018016 | 10/2016 |

(Continued)

OTHER PUBLICATIONS

Richter DE et al., Anal Chem 1996, 68, 1033.

(Continued)

*Primary Examiner* — Lyle Alexander
*Assistant Examiner* — Dwan A Gerido
(74) *Attorney, Agent, or Firm* — Philip Summa

(57) ABSTRACT

An energized dispersive extraction method for sample preparation for analysis is disclosed. The method includes the steps of placing an extraction solvent, sorbent particles, and a sample matrix containing an analyte in a heat conductive sample cup; positioning the sample cup in a pressure-resistant reaction chamber; dispersing the solvent and the sample matrix in the sample cup in the reaction chamber; heating the sample matrix and the solvent in the sample cup in the reaction chamber to a temperature that generates an above-atmospheric pressure; draining the solvent extract from the sample cup at atmospheric pressure; and collecting the solvent extract for analysis.

20 Claims, 2 Drawing Sheets

(56) References Cited

U.S. PATENT DOCUMENTS

| | | | |
|---|---|---|---|
| 5,601,707 | A | 2/1997 | Clay |
| 5,620,659 | A | 4/1997 | Revesz |
| 5,653,885 | A | 8/1997 | Jameson |
| 5,660,727 | A | 8/1997 | Gleave |
| 5,750,008 | A | 5/1998 | Lautenschlaeger |
| 5,785,856 | A | 7/1998 | Gleave |
| 5,858,178 | A | 1/1999 | Lautenschlaeger |
| 5,932,095 | A | 8/1999 | Walters |
| 6,048,457 | A | 4/2000 | Kopaciewicz |
| 6,086,767 | A | 7/2000 | Walters |
| 6,221,655 | B1 | 4/2001 | Fung |
| 6,794,127 | B1 | 9/2004 | Lafferty |
| 6,803,237 | B2 | 10/2004 | Manganini |
| 8,569,072 | B2 | 10/2013 | Halverson |
| 8,901,471 | B2 * | 12/2014 | Visinoni ............ B01D 11/0211 219/756 |
| 9,574,799 | B2 | 2/2017 | Buese |
| 9,739,692 | B2 | 8/2017 | Srinivasan |
| 2007/0275445 | A1 | 11/2007 | De Bont |
| 2011/0005932 | A1 | 1/2011 | Jovanovich |
| 2011/0233203 | A1 * | 9/2011 | Visinoni ............ B01D 11/0211 219/756 |
| 2013/0233093 | A1 | 9/2013 | Pohl |
| 2013/0316466 | A1 | 11/2013 | Srinivasan |
| 2013/0337132 | A1 | 12/2013 | Fenna |
| 2014/0114084 | A1 | 4/2014 | Hamler |
| 2014/0193303 | A1 | 7/2014 | Ellis |
| 2015/0119592 | A1 | 4/2015 | Hamler |
| 2015/0258521 | A1 | 9/2015 | McAdams |
| 2016/0303490 | A1 | 10/2016 | Ellis |
| 2016/0370035 | A1 | 12/2016 | Hofer |
| 2016/0370357 | A1 | 12/2016 | Lucas |

FOREIGN PATENT DOCUMENTS

| | | |
|---|---|---|
| CN | 107831252 | 3/2018 |
| DE | 2250933 | 5/1974 |
| EP | 0932355 | 8/1999 |
| EP | 2371437 | 10/2011 |
| EP | 3072568 | 9/2016 |
| FR | 2196831 | 3/1974 |
| GB | 380954 | 9/1932 |
| GB | 477567 | 1/1938 |
| GB | 530345 | 12/1940 |
| GB | 613568 | 11/1948 |
| GB | 683121 | 11/1952 |
| GB | 776938 | 6/1957 |
| GB | 845131 | 8/1960 |
| GB | 1012545 | 12/1965 |
| GB | 1065720 | 4/1967 |
| GB | 1074231 | 7/1967 |
| GB | 1123847 | 8/1968 |
| JP | H08029432 | 2/1996 |
| JP | H08338832 | 12/1996 |
| JP | 2005214785 | 8/2005 |
| JP | 2016101166 | 6/2016 |
| WO | 9325842 | 12/1993 |
| WO | 9627417 | 9/1996 |
| WO | 2008101670 | 8/2008 |
| WO | 2015160419 | 10/2015 |
| WO | 2018148225 | 8/2018 |

OTHER PUBLICATIONS

Definitions of "adsorption," "organic," "solvent," and "sorbent"—Lewis, Hawley'S Condensed Chemical Dictionary, 15th Edition, 2007, John Wiley & Sons.
EPA Method 3545 Pressurized Fluid Extraction (PFE), Rev. 1, Jan. 1998; pp. 10.
Definitions of "adsorb," "loose," "opposite," "sorbent," and "solid,"—Urdang, The Random House College Dictionary, Random House Inc. (1972).
EPA Method 3540C—Soxhlet Extraction, Rev. 3, Dec. 1996, pp. 8.
EPA Method 3550C—Ultrasonic Extraction, Revision 3, Feb. 2007; pp. 17.
EPA Method 8270D—Semivolatile Organic Compouns by Gas Chromatography/Mass Spectrometry (GC/MS), Rev. 4, Jan. 1998, pp. 62.
CRM Catalog No. 727 Base/Neutrals & Acids in Soil, ERA Environmental 2014 Proficiency Testing and Reference Materials, Online Product Catalog, Waters Corporation.
Knowles, D; Dorich, B; Carlson, R; Murphy, B; Francis, E; Peterson, J, Richter, B. "Extraction of Phthalates from Solid Liquid Matrices," Dionex Corporation, 2011, pp. 4.
Consumer Products Safety Commission, Test Method: CPSC-CH-C1001-09.3 Standard Operating Procedure for Determination of Phthalates Apr. 1, 2010; http://www.cpsc.gov/about/cpsia/ CPSC-CH-C1001-09.3.
Safety Data Sheet: Phthalates from Polyethlene in a CRM sample; SPEX CertiPrep CRM-PE001; Metuchen, NJ 08840, 2017; pp. 7.
Arsenault, J.C. Beginner's Guide to SPE Solid-Phase Extraction; 2012, Waters Corporation; pp. 28.
Lehotay, et al., Comparison of QuEChERS sample preparation methods for the analysis of pesticide residues in fruits and vegetables; Journ of Chromatography A, 1217 (2010) 2548-2560.
Kabay et al, Solvent-impregnated resins (SIRs)—Methods of preparation and their applications; Reactive & Functional Polymers 70 (2010) 484-496.
QuEChERS Simplified, Waters Corporation, Jul. 2016, pp. 8.
The Basics: QuEChERS Step by Step; 2013, accessed Dec. 8, 2016 at http://blog.telednetekmar.com/blog/bid/350968/The-Basics-QuEChERS-Step-by-Step.
AOAC Official Method 2007.01 Pesticide Residues in Food by Acetonitrile Extraction and Partitioning with Magnesium Sulfate, 2007 AOAC International, pp. 9.
Burns, Donald—Automated Sample Preparation, Anaytical Chemistry, vol. 53, No. 12, Oct. 1981.
Automated Protein and Peptide Sample Preparation for Mass Spec Analysis, Agilent Technologies, 2015, pp. 8.
Solid Phase Extraction, SPE Protocol—Sample Preparation; Orochem Technologies, Inc., 2016, pp. 5.
Co-pending U.S. Appl. No. 15/644,920 for "Rapid Sample Preparation for Analytical Analysis Using Dispersive Energized Extraction" filed Jul. 10, 2017.
Co-pending U.S. Appl. No. 15/644,938 for "Instrument for Analytical Sample Preparation" filed Jul. 10, 2017.
Jacketed vessels for all applications with flexibility to meet the most demanding design; AndersonDahlen Inc., Nov. 5, 2017; accessed Aug. 22, 2018 at https://web.archive.org/web/20171105035338/ https://www.andersondahlen.com/components/vessels/jacketed-vessels.
"I use a moka pot to make coffee every morning. I get coffee beans from Starbucks and it tastes good but how can I make it taste even better?" Published Jan. 16, 2015 on Quora.com; accessed at: https:// www.quora.com/I-use-a-moka-pot-to-make-coffee-every-morning-I-get-coffee-beans-from-Starbucks-and-it-tastes-good-but-how-can-I-make-it-taste-even-betterhttps://www.quora.com/.
Standard Operating Procedure for Soxhlet Extraction of Biomass; accessed Sep. 16, 2018 at https://pdfs.semanticscholar.org/presentation/ a96a/47d960bfbcde1f908239ccfaa8fc9d006b22.pdf; 12 pages.
Refluxing a Reaction; accessed Sep. 26, 2018 at http://cactus.dixie. edu/smblack/chemlabs/refluxing_a_reaction.pdf, 1 page.
Practical techniques in organic chemistry (Heating under reflux); accessed Sep. 21, 2018 at https://quizlet.com/137786055/161-practical-techniques-in-organic-chemistry-heating-under-reflex-flash-cards/; 2 pages.
Reflux and distillation posted Apr. 30, 2015 on ASSIST (Australian School Science Information Support for Teachers and Technicians); accessed Sep. 20, 2018 at https://assist.asta.edu.au/print/2802; 6 pages.
Ondruschka et al., Microwave-Assisted Extraction—A State-of-the-Art Overview of Varieties; Chimia 60 (2006); 321-325.
NEOS Microwave Soxhlet; Milestone brochure; date unknown; 6 pages.

(56) References Cited

OTHER PUBLICATIONS

Yunjie Ding et al., Determination of Pharmaceuticals in Biosolids using Accelerated Solvent Extraction and Liquid Chromatography/Tandem Mass Spectrometry; Journal of Chromatography A (2010); 24 pages.

ASE 200 Accelerated Solvent Extractor Operator's Manual, Doc. No. 031149, Rev. 4, Dec. 1999; 184 pages.

Frenich A.G. et al., "Determination of Pesticides in Food of Animal Origin" in Tadeo J.L. (Ed), "Analysis of Pestcides in Food and Environmental Samples," CRC Press, 2008, pp. 177-207.

Song, S. et al., "Development, comparison and application of sorbent-assisted accelerated solvent extraction, microwave-assisted extraction and ultrasonic-assisted extraction for the determinatioin of polybrominated diphenyl ethers in sediments," Journal of Chromatography A, 2016, vol. 1475, pp. 1-7.

How to Keep Grounds Out of Percolated Coffee_Percolator Coffee Pot [retrieved from internet on Jan. 11, 2018]<URL:https://web.archive.org/web/20160317210445/http://percolatorcoffeepot.org/how-to-keep-grounds-out-of-percolated-coffee/> published on Mar. 17, 2016 as per Wayback Machine.

Van Den Berg, C., In-situ product recovery from fermentation broths, 2010, Doctoral dissertation, TU Delft, Delft University of Technology, 117 pages.

Improved Soxhlet Extraction of Medical Marijuana Oil [viewed on internet on Jan. 7, 2019] < URL: https://www.youtube.com/watch?V=XOLJp8G732g>, published on May 15, 2013.

"General extraction time and solvent type for soxhlet extraction—can anyone help?" [accessed Jan. 7, 2019] < URL: https://www.researchgate.net/post/General- axtraction_time_and_solvent_type_for_soxhlet_extraction_can_anyone_help>, published 2013.

Dionex ASE Extraction Thimbles, Thermo Scientific, 2014; 4 pages.

\* cited by examiner

RAPID ENERGIZED DISPERSIVE SOLID PHASE EXTRACTION (SPE) FOR ANALYTICAL ANALYSIS

RELATED APPLICATIONS

This application is related to application Ser. No. 15/644,920 filed concurrently herewith for "Rapid Sample Preparation for Analytical Analysis Using Dispersive Energized Extraction;" and application Ser. No. 15/644,938 filed concurrently herewith for "Instrument for Analytical Sample Preparation."

BACKGROUND

The present invention relates to analytical chemistry, and in particular relates to sample preparation for molecular analysis.

Depending upon needs, attributes, or other factors, much analytical chemistry can be divided (for purposes of discussion) into elemental analysis and molecular analysis. Elemental analysis is necessary and useful and incorporates tools that range from simple combustion and acid digestion to sophisticated instrument techniques such as (among many others) various forms of atomic spectroscopy and several different uses of x-rays.

Although 118 elements have been shown to exist, only 94 occur naturally on earth, and only 88 in greater than "extreme trace" quantities. Going further, 10 elements make up 99.8% of the earth's crust. Thus, the search and analysis for elements present in compositions is generally well defined.

In contrast, molecular analysis—the task of identifying one or more compounds in a sample—presents an enormously larger set of possibilities. The number of "naturally occurring" compounds (those produced by plants or animals) is immeasurably large, and the capabilities of modern organic and inorganic synthesis have generated—figuratively or literally—a similar number of synthetic compounds.

Of such immense numbers of compounds, the large majority (particularly of synthetics) are limited to laboratory use and academic interest. Nevertheless, many compounds remain for which identification or quantitative measurement or both are helpful or necessary. Even a small group of recognizable representative samples would include pesticides in food, other synthetic chemicals in food (antibiotics, hormones, steroids), synthetic compositions (benzene, toluene, refined hydrocarbons) in soil, and undesired compositions in everyday items (e.g., Bisphenol-A ("BPA") in polycarbonate bottles and other plastic food packaging.

Identifying isolated molecular compounds is, using modern instrumentation, relatively straightforward. The typical tools include (but are not limited to) liquid or gas chromatography; visible, infrared, and ultraviolet spectroscopy; mass spectroscopy, and nuclear magnetic resonance ("NMR"). Once a molecular compound is identified, its concentration can often be determined based on known standards and calibration curves.

Because, however, these techniques require substantially pure isolated samples, some intermediate steps—generally referred to as "sample preparation"—must be carried out to isolate the compounds of interest (known or unknown) from the matrix (soil, plastic, food, etc.) in which they might be found and ready them for instrument analysis.

Based upon these and related factors, the market for molecular analysis is approximately 10 Limes that, of the market for elemental analysis.

In a general sense, extraction has been a main form of sample preparation; i.e., drawing one or more compounds of interest from a solid or a liquid (or a semi-solid) sample by mixing the sample with a solvent into which the desired compound(s) will move when given the opportunity.

For several generations (and continuing to date), sample preparation in the form of extraction has been carried out by the well-understood Soxhlet method which was invented in the 19th century Basically a single portion of solvent circulate repeatedly through a sample matrix until extraction is complete. To the extent the Soxhlet method has an advantage, it allows an extraction to continue on its own accord for as long as the boiling flask is heated and the condenser is cold.

In recent decades, advances in liquid chromatography have led to analogous uses of packed columns in a technique referred to as solid phase extraction ("SPE"). Originally, chromatography was used to separate fractions in mixed samples for analytical purposes, and indeed it still serves this purpose very well.

In SPE, the chromatography technique is modified to extract an analyte from a matrix. Nevertheless, SPE fundamentally remains a liquid chromatography technique in which molecules spread out (travel at different speeds) within a column based on their polarity, the particle size and polarity of the packed column (stationary phase), the polarity of the flowing liquid (mobile phase), the size (length and diameter) of the column and specific factors such as "hold-up volume," "linear velocity," and "flow rate." See, e.g., Arsenault, J. C. 2012. Beginner's Guide to SPE. Milford Mass.: Waters Corporation. (Arsenault 2012).

Although SPE is useful, it has limiting characteristics, some of which include the following factors. First, a proper description of SPE is "liquid-solid phase extraction" because the sample matrix that holds the analyte is almost always a liquid.

Second, because SPE is essentially a liquid chromatography technique, it requires either column packing steps or a new column for each test, along with a potential pre-swelling step depending upon the material selected or required for the stationary phase. SPE typically requires different methods and manipulative steps for different analytes, and the packing must be very tight to allow proper flow and avoid channeling.

Third, SPE must match the mobile phase and the stationary phase (the sorbent in the packed column) to the expected characteristics of the analyte.

Fourth, a more deliberate (slower) flow through the packed column tends to produce better separation among the fractions. Thus, in a very real sense slower SPE is better than faster SPE.

As potential further disadvantages, in some pressurized methods, suitable extraction cells must be strong enough to withstand the vapor pressure of the vaporized solvent as well as that generated by any breakdown products from the sample. Depending upon the circumstances, such cells must be relatively thick which increases their heating and cooling times during an extraction cycle.

Some individual extraction cells are formed of several sub-items and can be difficult to assemble correctly, a critical step for safety purposes. In some cases the design and structure of instruments that use such cells are more complex, and thus generally more costly, and in some cases subject to more vigilant safety measures, which again increases cycle times and costs.

Additionally, when extraction cells are attached to single inlets and outlets, any kind of countercurrent flow such as viscous mixing or bubbling can become difficult or impossible.

Finally, if additional pressure (i.e., in addition to simple gravity flow) is required to move solvent through the SPE column, an external pump or vacuum pull must be applied, which in turn adds some lesser or greater amount of complexity to the system and technique.

More recently, a dispersive solid phase extraction ("dSPE") method referred to as "QuEChERS" or "QuEChERS" ("quick-easy-cheap-effective-rugged-safe") has become a standard for extraction preparation of molecular samples. Dispersive SPE addresses some of the disadvantages of SPE, but still requires an extraction step, the adjustment of pHI with an appropriate ionic salt, is labor-intensive (even if advantageous compared to other methods), and requires two separate centrifuge steps.

QuEChERS is in many ways less complex than Soxhlet extraction, but still requires a multi-step process. In the literature, this is sometimes called a "three step process" (e.g., Paragraph 0153 of U.S. Patent Application Publication No. 20160370357), but in reality QuEChERS requires at least the following: homogenization of the matrix that contains the analyte of interest; adding extraction solvent and loose sorbent particles; hand agitation; buffering; a second agitation step; a centrifuge separation step; decanting; dispersive solid phase extraction ("dSPE") clean up; a second centrifuge separation step; and decanting the supernatant liquid following the centrifuge step.

In addition to the multi-step handling and transfer of the solvent, the sample, and the various mixtures, each of the centrifuge steps takes a recommended five minutes; so that the full QuEChERS sample preparation takes at least about 15-20 minutes. QuEChERS is also limited to room temperatures.

Accordingly, although the Soxhlet, SPE, and QuEChERS (dSPE) methods have their advantages, each remains relatively time-consuming. As a result, when multiple samples are required or desired to provide necessary or desired information, the time required to carry out any given extraction-based molecular preparation step reduces the number of samples that can be prepared in any given amount of time, thus reducing the amount of information available in any given time interval. To the extent that measurements, are helpful or necessary in a continuous process, this represents a longer gap between samples or before an anomalous or troublesome result can be identified.

In summary, among other disadvantages current sample preparation techniques are slow, require a large number of separate steps, use excess solvent, are difficult to automate, and operate under high liquid pressure.

Accordingly, a need continues to exist for efficient rapid extraction-based molecular preparation techniques.

SUMMARY

In a first aspect, the invention is a dispersive extraction based sample preparation method that includes the steps of placing an extraction solvent, sorbent particles, and a sample matrix that contains an analyte into a sample cup, and heating the sample cup, the sample matrix, the sorbent particles and the extraction solvent in a pressure-resistant chamber until the temperature generates an above-atmospheric pressure that together with the increased temperature drives the analyte substantially from the sample matrix into the extraction solvent while dispersing the sample matrix, the sorbent particles and the extraction solvent in the sample cup, and then releasing the solvent extract from the sample cup into a cooling tube at atmospheric pressure.

In another aspect, the invention is a dispersive extraction method for preparing analytes for molecular analysis, that includes the steps of adding a liquid sample matrix to a plurality of sorbent particles, potentially carrying an extraction solvent, in a sample cup, thereafter dispersing, heating, and pressurizing the solvent-carrying sorbent particles to extract the analyte from the heated liquid sample matrix and into the solvent carried by the sorbent particles, thereafter draining the pressurized heated liquid matrix at atmospheric pressure from the sample cup, thereafter adding a release solvent to the plurality of sorbent particles carrying the extraction solvent and the analyte, thereafter dispersing, heating, and pressurizing the release solvent and the sorbent particles to release the analyte into the release solvent, and thereafter draining the pressurized heated release solvent at atmospheric pressure.

In yet another aspect, the invention is a dispersive extraction method for preparing analytes for molecular analysis comprising collecting a cooled extraction solvent extract for analysis that has been drained from a sample cup after the extraction solvent, the sorbent particles and a sample matrix containing an analyte have been placed into the sample cup, and dispersed, heated, and pressurized, and the solvent extract has thereafter been cooled.

In yet another aspect, the invention is a heated pressurized dispersed mixture of an extraction solvent, sorbent particles, and a sample matrix containing an analyte in a sample cup in a pressure-resistant reaction chamber.

The foregoing and other objects and advantages of the invention and the manner in which the same are accomplished will become clearer based on the followed detailed description taken in conjunction with the accompanying drawings.

DETAILED DESCRIPTION

Figure 1:
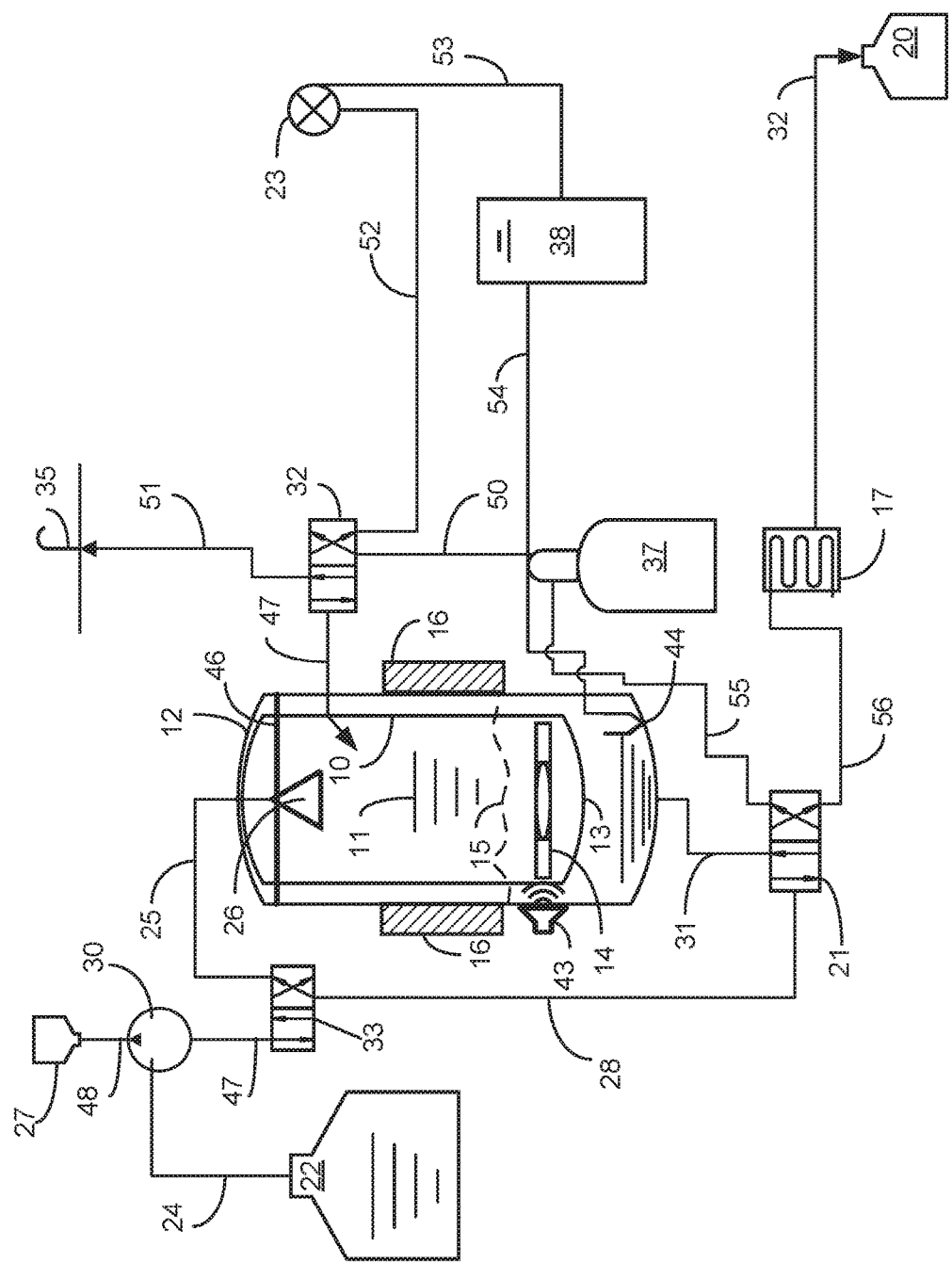
FIG. 1 is a schematic diagram of some of the elements used to carry out the method of the invention.

A number of terms are used herein to describe the method, some of which are listed here.

The term "solvent" is used in its well understood chemical sense; e.g., "a substance capable of dissolving another substance (solute) to form a uniformly dispersed mixture (solution) at the molecular or ionic size level." The adjective "organic" is used in its well understood sense to "embrace all compounds of carbon" other than certain small molecule combinations of carbon with oxygen, sulfur, and metals, and in some cases halogens. See, Lewis, HAWLEY'S CONDENSED CHEMICAL DICTIONARY, 15th Edition, 2007, John Wiley & Sons A "sample matrix" is the material to be tested for the presence and optionally the amount of analyte.

An "analyte" is the molecular compound of interest.

A "solvent extract" is the solution of analyte in a solvent following extraction.

A "sample cup" is the container for the sample matrix and the solvent.

A "pressure-resistant reaction chamber" is a compartment or closed space large enough to hold a selected sample cup and strong enough to withstand at least pressures generated by common extraction solvents heated above their boiling points.

The "collection vessel" is the container that collects the solvent extract following cooling.

The "filter" or "filter media" is the barrier in the cup or sample cup that holds the solid sample matrix, but that otherwise allows liquids to pass.

A "liquid sample matrix" is a sample in which the analyte is present in a liquid rather than a solid matrix.

"Absorption" refers to the penetration of one substance into the inner structure of another.

"Adsorption" refers to gathering one substance in condensed form on the surface of another substance. See, e.g., Lewis, HAWLEY'S CONDENSED CHEMICAL DICTIONARY 15th Edition John Wiley & Sons, Inc. (2007) and Urdang, THE RANDOM HOUSE COLLEGE DICTIONARY, Random House, Inc. (1972).

In that regard, the umbrella term "sorbent" will be used herein in its chemical dictionary sense as a substance that has a large capacity for absorbing moisture, gases, or other compositions. "A compound that absorbs, adsorbs, or entraps something." (Lewis).

As used herein, "solid" means matter that is "not liquid or gaseous," and that has "relative firmness, coherence of particles, or persistence of form" (Urdang).

As generally well understood by the skilled person, the term "disperse" describes an action that produces a dispersion. As set forth by Lewis, a dispersion is a two phase system in which one phase consists of finely divided particles distributed throughout a bulk substance with the particles being referred to as the dispersed phase and the bulk substance the external phase. In the context of the invention, the sample represents the dispersed phase and the extraction solvent represents the external phase. Depending upon the sample, the combination of sample and solvent also could be described as a mixture.

In a first aspect the invention is a dispersive extraction method for preparing samples for molecular analysis. In the method an extraction solvent, sorbent particles, and a sample matrix (i.e., that presumably contains an analyte of interest) are placed into a sample cup. Typical (but not limiting) sample matrices include solids such as food, food packaging, soil, liquids and semi-solids.

In the context of the invention, a typical sample cup is a cylinder formed of a heat-conductive, pressure-resistant material.

In the context of the invention, a typical sample cup is a cylinder form of a heat-conductive material. Because the sample cup 10 is inside the reaction chamber 12, it experiences little or no differential pressure, and thus its mass can be minimized to encourage thermal transfer. In current embodiments, an aluminum cylinder with a diameter of about 1.25 inches, about 3.5 inches long, and with wall thickness of about 0.01 inches thick has been found to be appropriate. As used herein, the term "heat conductive" is used in its well-understood sense to represent materials through which heat passes relatively quickly. Its opposite is, of course, the term "insulating," which is likewise well-understood as describing materials through which heat passes more slowly. On that basis, many metals and alloys are particularly useful for the vessel given that such conductivity is one of the distinguishing characteristics of most metals and alloys. Alternatively, many polymeric materials are considered insulating and ordinarily less helpful in the context of the invention. The thermal conductivities of many metals and alloys are published and widely disseminated, and an appropriate metal or alloy can be selected by the skilled person without undue experimentation.

An appropriate sample cup has an open mouth at one end and a partially open floor (e.g., a foraminous floor) at the opposite end. The partially open floor can support a filter or filter media and allow solvent extract to drain from the sample cup.

In the method of the invention, the sample matrix can also be described as loosely packed in the sample cup. Although the term "loose" is likewise relative, it is used here in in its normal sense as being free from anything that binds or restrains and free or released from fastening or attachment (Urdang, THE RANDOM HOUSE COLLEGE DICTIONARY, Random House Inc. (1972)). Because the sample matrix is loose, the addition of solvent from the top, the bottom, or both, helps disperse the sample matrix in the solvent.

As recognized by the skilled person (e.g., US EPA Method 3545) samples should be extracted using a solvent system that gives optimum, reproducible recovery of the analytes of interest from the sample matrix, at the concentrations of interest. The choice of extraction solvent depends on the analytes of interest and no single solvent is universally applicable to all analytes.

Typical (but not limiting) solid-liquid extraction solvents for molecular analysis include water, weak acids, weak bases, acetone, hexane, 2-propanol, cyclohexane, acetonitrile, methanol, and mixtures thereof.

Common solvents used for liquid/liquid extraction are ethyl acetate, methyl tertiary-butyl ether ("MTBE"), methylene chloride, hexane, and mixtures thereof.

The extraction solvent, the sorbent particles, and the sample matrix are mixed in the sample cup in the chamber. Mixing actions can include adding the solvent, creating a thermal gradient, or using the flow of a gas that is otherwise inert to the sample matrix, the analyte or the solvent. Those skilled in the extraction art will recognize that the gas can accordingly be selected based on the known parameters, and that in some cases compressed air will be appropriate while in others nitrogen or hydrogen may be best (with care based upon hydrogen's flammable characteristics), or in some cases one of the noble gases (e.g., helium, argon) may be best.

The sorbents are typically (although not exclusively) the same as or similar to those used in solid-liquid chromatography for conventional SPE or dispersive SPE. Silica and alumina and variations thereof are the most common, and in many cases carry functional groups bonded to their surface. Alumina can be pre-treated to create acidic ("A"), basic ("B"), or pH neutral ("N") slurries in water. Functional groups often include various forms of amines or hydrocarbons, with "PSA" (primary-secondary amine) and "C18" (octadecylsilylated silica gel) being frequent choices.

The skilled person is familiar with sorbent choices and can select them as desired or necessary and without undue experimentation.

Other mixing techniques can be used (e.g., magnetic stirrers or other mechanical devices), but will require more complex instrumentation.

The sample matrix, the sorbent particles, and the solvent are then heated in the sample cup in a reaction chamber to a temperature at which evaporated solvent generates an above-atmospheric pressure. A temperature of 50° C.-150°

C. is exemplary depending upon the lability or stability of the sorbent and analyte(s) at particular temperatures. At these temperatures, typical organic extraction solvents generate a corresponding pressure of 50-250 pounds per square inch (psi). In experiments to date, the time to reach this temperature is about 90 seconds, at which point extraction is substantially complete (it being understood that extraction is an equilibrium process). The pressure generated by the solvent vapor is then used to drain the solvent extract from the sample cup into a cooling coil that has a length sufficient to reduce the temperature of the extract to near ambient (e.g., 25° C.) while the solvent extract is in the coil. Stated differently, the release of the solvent extract to atmospheric pressure drives the solvent extract into the cooling tube. The solvent extract is then collected from the coil, typically in a collection vessel. In exemplary experiments, metal tubing with a length of about 10 feet tends to provide a dwell time of about 30 seconds, which is sufficient to cool the solvent extract to ambient or near-ambient temperature. Thus, the coil is typically used for space saving purposes, but a coil shape is optional rather than mandatory.

The sample matrix, the sorbent particles, and the extraction solvent can be added in amounts that are typical in this field. For example, a solid matrix is collected in a manner that provides between about 0.5 to 10 grams (g) of the sample matrix of interest. The amount of extraction solvent will be proportional; typically about 5-100 milliliters (mL). The amount of sorbent particles will typically be in the 0.5-5 g range with 50 about 1 g being common.

Although "disposable" is in a sense a user's choice the sample cup can be used with a filter, and in most cases the modest cost of the filter will permit—or the nature of the extraction may require—the user to incorporate a new, fresh filter for every extraction depending upon the economics of a particular proactive and the choice of a reaction vessel material, even the sample cup itself can be considered disposable.

FIG. 1 illustrates a number of the features of the method in the context of a schematic diagram. FIG. 1 illustrates a heat-conductive sample cup 10 surrounded by a pressure resistant reaction chamber 12. The combination of extraction solvent, sorbent particles and the sample matrix that contains an analyte (schematically diagrammed by the horizontal lines 11) are maintained in the sample cup 10 using the one open and filtered end 13. The filter medium is designated at 14.

FIG. 1 also shows that additional extraction solvent optionally can be added to the reaction chamber 12 outside of the sample cup 10 as indicated by the dotted line 15 to jacket the sample cup 10.

A heater 16 heats the solvent 15 in the reaction chamber 12 outside of the sample cup 10 to in turn heat the sample cup 10, the sample matrix 11, the sorbent particles, and the extraction solvent until the temperature generates an above-atmospheric pressure that together with the increased temperature drives the analyte substantially from the sample matrix into the extraction solvent.

The solvent extract is then released by opening the sample cup and reaction chamber to atmospheric pressure at the open end (e.g., using valve 21) so that the solvent extract can travel to a cooling tube 17 which has a length sufficient to cool the solvent extract to ambient or near-ambient temperatures so that the cooled solvent extract can be collected ready for analysis, for example in a collection vessel 20.

FIG. 1 is a schematic diagram of the basic elements of an instrument to carry out the method steps of the present invention. In FIG. 1, the sample cup is illustrated at 10, and is shown as positioned in the thermally conductive pressure-resistant heating chamber 12.

In carrying out preparation of a sample for molecular analysis, the sample matrix and the sorbent particles are placed in the sample cup 10 which is then placed in the reaction chamber 12. A solvent from a supply 22 (or several such supplies) is delivered to the sample cup 10 (and thus to the sample matrix) through a rotary valve 30, metered in a syringe pump 30, returned through the rotary valve 30, then to the valve 33, the associated passageways 24 and 25, and a delivery head 26. A liquid matrix sample can be delivered in the same manner.

FIG. 1 also illustrates that the gas agitation is carried out by delivering an inert gas from a supply 37 to a position at or near the bottom of the sample cup using the passageways 40 and 41, as controlled by the valve 42. If a secondary agitation is required, it can be carried out with a device such as an ultrasonic generator 43 which would typically be a piezoelectric transducer.

The draining step takes place when the valve 21 is opened to atmospheric pressure so that the pressurized solvent vapor in the reaction chamber 30 pushes the liquid solvent extract out through the passageway 31, then through the valve 21, and then cooling coil 17. The cooling coil is connected to a collection vessel 20 by the collection tube 32.

A thermocouple 44 and a pressure gauge 23 can be used to accurately determine the temperature in the sample cup 10 in relation to the vapor pressure of the selected extraction solvent. In particular, a correlations can be developed between solvent temperature and vapor pressure. As schematically illustrated in FIG. 1, a processor 38 can be used for this purpose. Thereafter, vapor pressure can be measured to indicate solvent temperature in the sample cup 10 with a high degree of accuracy.

As a further advantage, because this embodiment seals the sample cup 10 in the reaction chamber 12, the system can also be pre-pressurized (for example up to about 25 pounds per square inch) in the headspace (i.e., the gas above the solvent and sample) with air or an inert gas (i.e., a gas inert to the sample and to the extraction solvent) to help force the hot liquid solvent to a higher temperature before the solvent generates the desired vapor pressure. Keeping the solvent in the liquid state also helps with the desired the thermal transfer inside and outside of the reaction vessel. Perhaps just as importantly, a higher pressure in the headspace helps ensure that all of the extraction solvent is pushed from the sample cup 10, through any filter media 14, and thereafter to the cooling coil 17.

A gas valve 32 can vent the system (e.g., to vent 35), or direct gas for pressure measurement at the gauge 23, or direct inert gas from the source 37 into the reaction vessel 10.

Further to FIG. 1 and to complete the description of the possibilities, solvent can flow from the solvent supply 22 to the rotary valve 30 through the line 24. The line 47 connects the rotary valve 30 with the auxiliary valve 33. The line 28 connects the auxiliary valve 33 to the gas valve 21 which in turn can use the line 31 to deliver solvent to the bottom of the reaction chamber 12.

The line 48 connects the rotary valve 30 to the syringe 40 so that liquids from the supply 22 can be metered into the syringe 40 from the supply 22 and thereafter from the syringe 40 into the sample cup and through the lines 35 to 25 and the dispenser head 26. The clotted line 15 represents the position of solvent between the sample cup 10 and the reaction chamber 12 when the solvent is used to jacket the sample cup 10.

The gas supply 37 can supply extra pressure to the headspace through the lines 50 and 47 which, along with the gas flow to several other items, is controlled by the valve 32. The line 51 joins the valve 32 to the vent 35.

As part of the gas pressure monitoring, the line 52 connects the valve 32 to the pressure gauge 23 and the pressure gauge 23 is wired to the processor 38 through the communication line 53. The processor 38 is also connected to the thermocouple 44 using the communication line 54 so that monitored combinations of temperature and vapor pressure for various sample extractions can be used to develop helpful standardized information.

In order to provide agitating gas into the bottom of the reaction chamber 12 and the sample cup 10, the gas supply at 37 is also connected to the valve 21 through an appropriate line or tube 184.

A pressure head seal 46 seals the sample cup in the reaction chamber. Line 56 drains solvent from valve 21 to the coil 17, and line 32 drains the coil 17 to the collection vessel 46.

The nature of the method is such that it can be expressed in some additional aspects. In a second aspect, the steps include placing an extraction solvent, sorbent particles, and the sample matrix containing the analyte into a sample cup. Thereafter, the sample matrix, sorbent particles and the extraction solvent are dispersed, heated, and pressurized in the supported sleeve to extract the analyte from the heated sample matrix and into the heated organic solid. The pressurized heated extraction solvent extract is then drained at atmospheric pressure from the sample cup until the drained extraction solvent extract approaches or reaches ambient temperature. The cooled extraction solvent extract is then collected for analysis.

In various embodiments, excellent results have been obtained by carrying out the initial dispersion (or agitation) step (i.e., with the inert gas) before carrying out the heating and pressurizing steps. Such dispersion can be driven by adding the solvent, temperature gradients, adding an inert gas, or ultrasonic vibration.

Expressed as yet another aspect, the invention is a dispersive extraction based sample preparation method that includes the step of placing a solvent, sorbent particles, and a sample matrix that contains an analyte into a sample cup, with the improvement steps of heating the vessel, the sample matrix, the sorbent particles, and the solvent in a pressure resistant chamber until the temperature generates an above atmospheric pressure that together with the increased temperature drives the analyte substantially from the sample matrix into the solvent. The method includes a step of dispersing the sample matrix, the sorbent particles and the solvent in the vessel followed by releasing the solvent extract from the sample cup into a cooling tube at atmospheric pressure, and in which the cooling tube has a length sufficient to substantially cool the solvent extract to ambient or near-ambient temperatures, and then collecting the cooled solvent extract for analysis.

In another aspect, the extraction method can be carried out slightly differently, particularly on liquid matrices that include the analyte of interest. In this aspect, the method includes the steps of adding a liquid sample matrix to a plurality of particles that can optionally carry an extraction solvent. Such particles are also referred to as solvent impregnated resins ("SIRs"). The particles are positioned in the sample cup after which the particles and the liquid matrix are dispersed, heated, and pressurized in the reaction vessel to extract the analyte from the heated liquid sample matrix and into the solvent carried by the particles.

Thereafter the pressurized heated liquid matrix is drained by opening the chamber to atmospheric pressure.

In the next step, a release solvent is added to the porous particles carrying the extraction solvent and the analyte. The dispersing, heating and pressurizing steps are repeated for the release solvent and the particles to release the analyte into the release solvent. The release solvent is then drained by opening the thermally conductive chamber to atmospheric pressure to allow the release solvent to travel in the cooling tube until the drained release solvent reaches ambient or near-ambient temperature, after which it is collected for analysis.

Appropriate particles are generally well understood in the art and are typically formed of a physically durable water insoluble polymer resin in a mesh size (or range of mesh sizes) that will be retained by the porous sleeve, and typically with a broad distribution in pore sizes. The polymer should, of course, remain stable at the temperatures and pressures generated in the extraction steps.

Typical particles are formed from resins such as hydrophobic cross-linked polystyrene copolymer resins; polymers based on styrene cross-linked with divinyl benzene, and polymerized methacrylic acid ester. See, e.g., Kabay et al, *Solvent—impregnated resins (SIRs)—Methods ofpreparation and their apphcations*; Reactive & Functional Polymers 70 (2010) 484-496. As in the case of the sorbent particles, the skilled person is familiar with and can select appropriate resins without undue experimentation.

As in the other aspects of the invention, the dispersing step is often helpful if it precedes the heating and pressurizing steps, and if a second step is needed, it is carried out concurrently with the heating and pressurizing steps.

As in the previous embodiments, the step of draining the release solvent includes draining the heated release solvent in a coil that has a length sufficient to cool the drained release solvent to approach or reaching ambient temperature while the release solvent is in the coil. At that point, the release solvent containing the analyte is at a temperature ready for molecular analysis in conventional equipment.

Basically, the method of the invention is appropriate for preparing any analyte that is stable at the expected temperatures and pressures.

Some examples of analytes for which the methods described herein are suitable include pesticides, pesticide residues, aromatic and aliphatic compounds such as: benzene, toluene, ethyl benzene, xylene(s), cumene, limonene, nitrobenzene, cresol(s), higher alkylated phenols, octanol, nonanol, decanol, hexane, heptane, methyl isobutyl ketone (MIBK), tetrahydrothiophene, cs2, tetramethyltetrahydrofuran, and methyl tert-butyl ether (MTBE), among others.

The invention can also prepare samples containing halogenated/chlorinated compounds such as monochloromethane, dichloromehane, trichloromethane, tetrachloromethane, dichloroethane (1,1 & 1,2), trichloroethane, tetrachloroethane, chloroethylene, dichloroethylene, trichloroethylene, tetrachloroethylene, trichloropropane, chlorobutadiene, hexachlrobutadiene, monochlorobenzene, dichlorobenzen, chlorobenzenes, chloroaphtalene, hexachlorocyclohexane, monochlorophenol, dichlorophenol, trichlorophenol, dichloro-di-isopropylether, and dioxins.

The invention can also prepare samples containing polyaromatic hydrocarbons such as PCBs, naphthalene, acenaphtylene, acenaphthene, flourene, phenanthrene, anthracene, flouranthene, pyrene, benz(a) antharacene, chrysene, and dibenzothiophene.

In another aspect, the method can be expressed as collecting a cooled extraction solvent extract for analysis that has been drained from a foraminous portion of a rigid outer liner support that together with a rigid inner liner support holds a porous sleeve liner, and after the extraction solvent, sorbent particles, and a sample matrix containing an analyte have been placed into the porous sleeve liner, and dispersed, heated, and pressurized, and the solvent extract has thereafter been cooled.

In each embodiment, solvents can be selected from the group consisting of water, weak acids, weak bases, ethyl acetate, methyl tertiary-butyl ether ("MTBE"), methylene chloride, hexane, acetone, 2-propanol, cyclohexane, acetonitrile, methanol and mixtures thereof, but are not limited to that particular group.

Each embodiment can use an ultrasonic second dispersion or agitation step during the pressurized heating step.

In each embodiment, the release of the solvent extract to atmospheric pressure is used to drive the solvent extract into the cooling tube.

In each embodiment, the porous sleeve liner forms a barrier that ultimately maintains either a solid matrix, or the solvent impregnated particles in the sample cup.

In each embodiment, representative heating temperatures are 50-150° C. and representative resulting pressures are between about 50 and 250 psi.

In yet another aspect, the invention can be expressed as the heated pressurized dispersed mixture of an extraction solvent, sorbent particles, and a sample matrix containing an analyte in a porous sleeve liner supported between a rigid inner liner support and a rigid outer liner support.

EXPERIMENTAL

Example 3—Extraction of Pesticides from Soybeans

In another aspect, the invention provides an improvement upon the dispersive SPE ("dSPE") method referred to in the art as QuEChERS. QuEChERS is an accepted extraction and matrix clean up procedure for multi-residue analytes in a variety of different matrices. The invention is an alternative option to QuEChERS that offers comparable results easily, quickly and reliably, and that has the additional capacity for elevated temperatures (QuEChERS being limited to room temperature).

| Method | Time (min) | Automated |
|---|---|---|
| Invention | 5 | Yes |
| QuEChERS | 20 | No |

The invention is both faster than QuEChERS and automated, creating a more efficient lab.

Example 3 compared the invention against the AOAC 2007.01 9 (QuEChERS) Procedure, which includes the following steps:

Sample Extraction
1. Transfer 10-15 g of homogenized sample to 50 mL centrifuge tube;
2. Per 15 g sample, add 15 mL 1% acetic acid in acetonitrile plus contents of acetate tube
3. Shake vigorously for 1 min.;
4. Centrifuge at above 1500 U/min for 1 min.

Sample Cleanup
1. Transfer 1 ml, of acetonitrile layer to a dSPE 2 ml, tube;
2. Shake vigorously for 1 min;
3. Centrifuge at above 1500 U/min for 1 min;
4. Transfer the supernatant to a CC vial for concurrent GCMS analysis.

The entire process takes around 20 minutes of constant manual work.

Example 3: In the invention, sample extraction and sample clean up are carried out together:
1. Transfer the homogenized food sample to the sample cup and add dSPE sorbent;
2. Place the sample cup in the pressure-resistant reaction chamber;
3. Carry out the steps described herein;
4. Transfer the solvent extract to a GC vial for concurrent GC-MS analysis.

The entire process takes only 5 min per sample and can be automated.

Example 3

| Pesticide | Method | Recovery (%) |
|---|---|---|
| Cyprodinil | Example 3 | 90 |
| Cyprodinil | QuEChERS | 95 |
| Cyprodinil | QuEChERS | 85 |
| Chlorpyrifos | Example 3 | 125 |
| Chlorpyrifos | QuEChERS | 98 |

Figure 2:
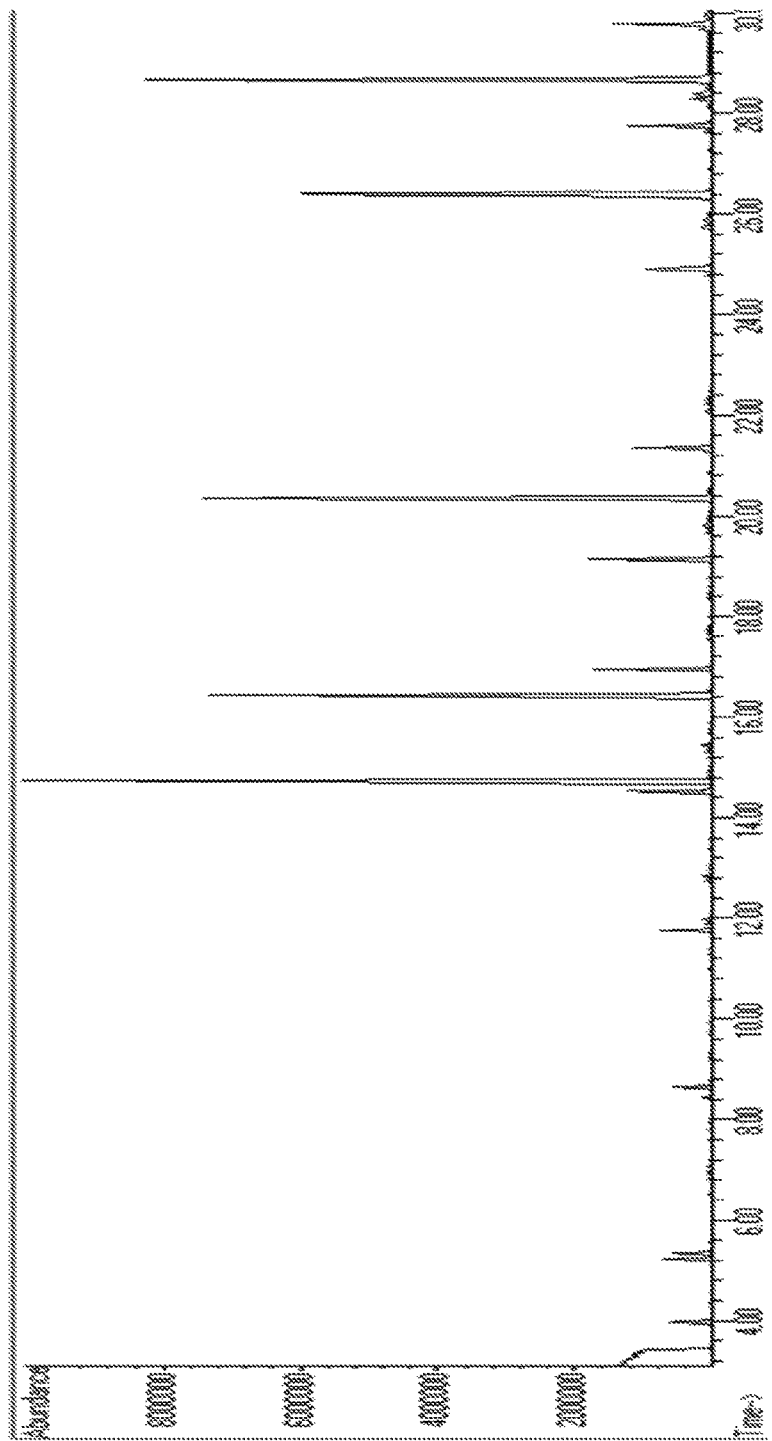
FIG. 2 is a full scan chromatogram of the results of the Example 3 soybean extraction carried out using the method of the invention.

Table 5 is a comparison of the invention's Example 3 results to the QuECh ERS results for the extraction of pesticides from soybeans. The QuEChERS data is based on published recoveries for AOAC method 2001.01 (Journal of Chromatography A, 1271 (2010) 2548-2560). The invention (Example 3) achieved comparable results to those published. In comparison, QuEChERS data can vary widely due to the manual nature of the procedure FIG. 2 is a full scan chromatogram of the results of the Example 3 soybean extraction carried out using the method of the invention.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A dispersive extraction based sample preparation method comprising:
   placing liquid extraction solvent, sorbent particles, and a sample matrix that contains an analyte into a heat conductive sample cup surrounded by a pressure-resistant reaction chamber with the heat conductive sample cup having one opened filtered end opening into the reaction chamber;
   adding liquid extraction solvent to both the inside of the sample cup and to the reaction chamber outside of the sample cup;
   heating the liquid extraction solvent in the reaction chamber outside of the sample cup to in turn heat the sample cup, the sample matrix, the sorbent particles and the liquid extraction solvent until the temperature generates an above-atmospheric pressure that together with the increased temperature drives the analyte substantially from the sample matrix into the liquid extraction solvent; and draining the liquid solvent extract from the sample cup through the one open filtered end into a cooling tube at atmospheric pressure.

2. A dispersive extraction based sample preparation method according to claim 1 wherein:

the draining step is carried out until the drained liquid extraction solvent approaches or reaches ambient temperature; and thereafter collecting the cooled release solvent for analysis.

3. A dispersive extraction based sample preparation method according to claim 1 further comprising dispersing the sample matrix, the sorbent particles and the liquid extraction solvent in the sample cup.

4. A dispersive extraction based sample preparation method according to claim 1 further comprising adding an inert gas to the reaction chamber to increase the total pressure.

5. A dispersive extraction based sample preparation method according to claim 1 comprising heating a thermally responsive reaction chamber to in turn heat the sample cup, the liquid extraction solvent, the sorbent particles and the sample matrix.

6. A dispersive extraction based sample preparation method according to claim 1 comprising heating the sample matrix, the sorbent particles and the liquid extraction solvent to a temperature of between about 50° C. and 150° C. and generating a resulting pressures of between about 50 and 250 psi.

7. A dispersive extraction based sample preparation method according to claim 1 wherein the liquid extraction solvent is selected from the group consisting of water, weak acids, weak bases, ethyl acetate, methyl tertiary-butyl ether ("MTBE"), methylene chloride, hexane, acetone, 2-propanol, cyclohexane, acetonitrile, methanol and mixtures thereof.

8. A dispersive extraction based sample preparation method according to claim 1 further comprising adding buffering salts to the sample cup prior to the step of heating the sample cup.

9. A dispersive extraction based sample preparation method according to claim 1 further comprising molecular analysis of the cooled liquid solvent extract with the analysis being selected from the group consisting of mass spectrometry, gas chromatography mass spectroscopy, ultraviolet spectroscopy, infrared spectroscopy, nuclear magnetic resonance spectroscopy, and successive or concurrent uses of each.

10. A dispersive extraction based sample preparation method according to claim 1 wherein the step of placing the sorbent particles into a sample cup with a liquid extraction solvent and a sample matrix comprises placing particles selected from the group consisting of silica, silica particles with functional groups bonded to their surface alumina, alumina particles with functional groups bonded to their surface, alumina pre-treated to create acidic, basic, or pH neutral slurries in water, and combinations thereof.

11. A dispersive extraction based sample preparation method comprising:

placing a liquid extraction solvent, sorbent particles, and a liquid sample matrix that contains an analyte into a sample cup surrounded by a pressure-resistant reaction chamber with the heat conductive sample cup having one opened filtered end;

adding liquid extraction solvent to both the inside of the sample cup and to the reaction chamber outside of the sample cup;

heating the liquid extraction solvent in the reaction chamber outside of the sample cup to in turn heat the sample cup, the sample matrix, the sorbent particles and the liquid extraction solvent until the temperature generates an above-atmospheric pressure that together with the increased temperature drives the analyte substantially from the sample matrix into the extraction solvent in the sorbent particles;

thereafter draining the pressurized heated liquid matrix at atmospheric pressure from the sample cup and the reaction chamber;

thereafter adding a liquid release solvent to both the inside of the sample cup and to the reaction chamber outside of the sample cup, and to the plurality of sorbent particles carrying the liquid extraction solvent and the analyte in the sample cup;

thereafter, heating, and pressurizing the liquid release solvent and the sorbent particles to release the analyte into the liquid release solvent; and thereafter draining the pressurized heated liquid release solvent at atmospheric pressure.

12. A dispersive extraction method according to claim 11 wherein:

the draining step is carried out until the drained liquid release solvent approaches or reaches ambient temperature; and thereafter collecting the cooled release liquid solvent for analysis.

13. A dispersive extraction method according to claim 11 wherein the sorbent particles are formed of a physically durable water-insoluble polymer resin, in a mesh size retained by the sample cup, with a broad distribution of pore sizes and that remains stable at the temperatures and pressures generated in the extraction steps.

14. A dispersive extraction method according to claim 11 wherein the sorbent particles are formed of a resin selected from the group consisting of hydrophobic crosslinked polystyrene copolymer resin; polymers of styrene crosslinked with divinylbenzene; and polymerized methacrylic acid ester.

15. A dispersive extraction based sample preparation method according to claim 11 further comprising dispersing the sample matrix, the sorbent particles and the liquid extraction solvent in the sample cup.

16. A dispersive extraction method according to claim 11 wherein the dispersing step precedes the heating and pressurizing steps.

17. A dispersive extraction method according to claim 11 wherein the dispersing step comprises feeding a gas that is inert to the liquid extraction solvent, the particles and the analyte into the sample cup.

18. A dispersive extraction method according to claim 12 wherein the step of draining the pressurized heated liquid release solvent at atmospheric pressure comprises draining the heated liquid release solvent into a coil with a length sufficient to cool the drained liquid release solvent to approach or reach ambient temperature in the coil.

19. A dispersive extraction method according to claim 11 wherein the liquid extraction solvent in the particles is selected from the group consisting of water, weak acids, weak bases, ethyl acetate, methyl tertiary-butyl ether ("MTBE"), methylene chloride, hexane, acetone, 2-propanol, cyclohexane, acetonitrile, methanol and mixtures thereof.

20. A dispersive extraction method according to claim 11 comprising heating the sample matrix, the sorbent particles and the liquid extraction solvent to a temperature of between about 50° C. and 150° C. and generating a resulting pressure of between about 50 and 250 psi.

\* \* \* \* \*